(12) United States Patent
Christensen et al.

(10) Patent No.: US 8,500,825 B2
(45) Date of Patent: Aug. 6, 2013

(54) PROSTHETIC FOOT WITH FLOATING FOREFOOT KEEL

(75) Inventors: Roland J. Christensen, Gunnison, UT (US); Alexandre E. Guerinot, Phoenix, AZ (US)

(73) Assignee: Freedom Innovations, LLC, Irvine, CA (US)

( * ) Notice: Subject to any disclaimer, the term of this patent is extended or adjusted under 35 U.S.C. 154(b) by 324 days.

(21) Appl. No.: 12/826,174

(22) Filed: Jun. 29, 2010

(65) Prior Publication Data

US 2011/0320012 A1 Dec. 29, 2011

(51) Int. Cl.
*A61F 2/66* (2006.01)

(52) U.S. Cl.
USPC .......................................................... 623/55

(58) Field of Classification Search
USPC ...................................................... 623/52, 55
See application file for complete search history.

(56) References Cited

U.S. PATENT DOCUMENTS

| | | | |
|---|---|---|---|
| 42,799 A | 5/1864 | Shepard |
| 92,031 A | 6/1869 | Foster |
| 292,800 A | 2/1884 | Furrer |
| 497,026 A | 5/1893 | Judson |
| 1,001,641 A | 8/1911 | Harrison |
| 1,191,633 A | 7/1916 | White |
| 1,289,580 A | 12/1918 | Vincenti |
| 1,354,427 A | 9/1920 | Welter |
| 1,779,765 A | 10/1930 | Eichhorn |
| 1,996,874 A | 4/1935 | Mascau |
| 2,036,830 A | 4/1936 | Rowley |
| 2,050,973 A | 8/1936 | Kurtz |
| 2,101,265 A | 12/1937 | Mercier |
| 2,379,538 A | 7/1945 | Meierhofer |
| 2,443,356 A | 4/1946 | Mathis |
| 2,453,969 A | 4/1947 | Carter |
| 2,570,735 A | 3/1949 | Weise |
| 2,470,480 A | 5/1949 | Fogg |
| 2,617,115 A | 7/1949 | Ellery |
| 2,640,200 A | 7/1950 | Wisbrun |
| 2,843,853 A | 11/1956 | Mauch |
| 2,973,969 A | 3/1961 | Thall |
| 3,206,235 A | 9/1965 | Albernson |
| 3,379,430 A | 4/1968 | Ransom |
| 3,548,420 A | 12/1970 | Spence |
| 3,551,914 A | 1/1971 | Woodall |
| 3,754,286 A | 8/1973 | Ryan |

(Continued)

FOREIGN PATENT DOCUMENTS

| | | |
|---|---|---|
| BR | 9304552 | 7/1995 |
| CA | 2266113 | 10/1999 |

(Continued)

OTHER PUBLICATIONS

PCT Application PCT/US2011/043649; filing date Jul. 12, 2011; International Search Report mailed Feb. 9, 2012.

(Continued)

*Primary Examiner* — David H Willse
(74) *Attorney, Agent, or Firm* — Thorpe North & Western LLP (57) ABSTRACT

A prosthetic foot device has an elongate forefoot spring carried by a fastener and suspended between upper and lower bumpers. A heel spring is suspended between an end of the fastener and the lower bumper.

21 Claims, 4 Drawing Sheets

U.S. PATENT DOCUMENTS

| | | | |
|---|---|---|---|
| 3,858,379 | A | 1/1975 | Graves et al. |
| 3,871,032 | A | 3/1975 | Karas |
| 3,874,004 | A | 4/1975 | May |
| 3,906,552 | A | 9/1975 | Weber |
| 3,920,610 | A | 11/1975 | Wagner |
| 3,956,775 | A | 5/1976 | Moore |
| 3,982,280 | A | 9/1976 | Asbelle et al. |
| 4,089,072 | A | 5/1978 | Glabiszewski |
| 4,328,594 | A | 5/1982 | Campbell et al. |
| 4,341,222 | A | 7/1982 | Gardineer et al. |
| 4,364,128 | A | 12/1982 | Mummert |
| 4,370,761 | A | 2/1983 | Serri |
| 4,442,554 | A | 4/1984 | Copes |
| 4,499,613 | A | 2/1985 | Yarrow |
| 4,506,395 | A | 3/1985 | Haupt |
| 4,517,968 | A | 5/1985 | Greene et al. |
| 4,547,913 | A | 10/1985 | Phillips |
| 4,606,332 | A | 8/1986 | Gibson |
| 4,636,220 | A | 1/1987 | Ziegelmeyer |
| 4,645,509 | A | 2/1987 | Poggi et al. |
| 4,676,800 | A | 6/1987 | Chen |
| 4,676,801 | A | 6/1987 | Lundeen |
| 4,688,559 | A | 8/1987 | Vito et al. |
| 4,721,510 | A | 1/1988 | Cooper et al. |
| 4,764,172 | A | 8/1988 | McCoy |
| 4,793,450 | A | 12/1988 | Savenije |
| 4,822,363 | A | 4/1989 | Phillips |
| 4,852,863 | A | 8/1989 | Breitenbacher et al. |
| 4,865,611 | A | 9/1989 | Al-Turaiki |
| 4,865,612 | A | 9/1989 | Arbogast et al. |
| 4,869,476 | A | 9/1989 | Shtarkman |
| 4,892,553 | A | 1/1990 | Prahl |
| 4,938,775 | A | 7/1990 | Morgan |
| 4,938,777 | A | 7/1990 | Mason et al. |
| 4,959,073 | A | 9/1990 | Merlette |
| 4,986,393 | A | 1/1991 | Preukschate et al. |
| 5,007,938 | A | 4/1991 | Prahl |
| 5,019,109 | A | 5/1991 | Voisin |
| 5,030,239 | A | 7/1991 | Copes |
| 5,037,444 | A | 8/1991 | Phillips |
| 5,062,859 | A | 11/1991 | Naeder |
| 5,088,479 | A | 2/1992 | DeToro |
| 5,112,356 | A | 5/1992 | Harris et al. |
| 5,116,383 | A | 5/1992 | Shorter et al. |
| 5,116,384 | A | 5/1992 | Wilson et al. |
| 5,156,632 | A | 10/1992 | Wellershaus |
| 5,181,932 | A | 1/1993 | Phillips |
| 5,181,933 | A | 1/1993 | Phillips |
| 5,217,500 | A | 6/1993 | Phillips |
| 5,219,324 | A | 6/1993 | Hall |
| 5,219,365 | A | 6/1993 | Sabolich |
| 5,226,875 | A | 7/1993 | Johnson |
| 5,258,039 | A | 11/1993 | Goh et al. |
| 5,267,633 | A | 12/1993 | Endo et al. |
| 5,290,319 | A | 3/1994 | Phillips |
| 5,314,499 | A | 5/1994 | Collier, Jr. |
| 5,376,133 | A | 12/1994 | Gramnas |
| 5,376,139 | A | 12/1994 | Pitkin |
| 5,376,141 | A | 12/1994 | Phillips |
| 5,387,246 | A | 2/1995 | Phillips |
| 5,405,411 | A | 4/1995 | McCoy |
| 5,425,781 | A | 6/1995 | Allard et al. |
| 5,425,782 | A | 6/1995 | Phillips |
| 5,443,528 | A | 8/1995 | Allen |
| 5,443,529 | A | 8/1995 | Phillips |
| 5,449,150 | A | 9/1995 | Watanabe et al. |
| 5,458,656 | A | 10/1995 | Phillips |
| 5,464,441 | A | 11/1995 | Phillips |
| 5,482,513 | A | 1/1996 | Wilson |
| 5,486,157 | A | 1/1996 | DiBenedetto |
| 5,486,209 | A | 1/1996 | Phillips |
| 5,507,838 | A | 4/1996 | Chen |
| 5,509,936 | A | 4/1996 | Rappoport et al. |
| 5,509,937 | A | 4/1996 | Allard et al. |
| 5,509,938 | A | 4/1996 | Phillips |
| 5,514,185 | A | 5/1996 | Phillips |
| 5,514,186 | A | 5/1996 | Phillips |
| 5,545,127 | A | 8/1996 | DeToro |
| 5,549,714 | A | 8/1996 | Phillips |
| 5,571,210 | A | 11/1996 | Lindh |
| 5,571,213 | A | 11/1996 | Allen |
| 5,593,455 | A | 1/1997 | Phillips |
| 5,593,456 | A | 1/1997 | Merlette |
| 5,593,457 | A | 1/1997 | Phillips |
| 5,609,568 | A | 3/1997 | Andrews |
| 5,645,138 | A | 7/1997 | Tajima et al. |
| 5,653,767 | A | 8/1997 | Allen et al. |
| 5,653,768 | A | 8/1997 | Kania |
| 5,695,526 | A | 12/1997 | Wilson |
| 5,701,686 | A | 12/1997 | Herr et al. |
| 5,725,598 | A | 3/1998 | Phillips |
| 5,728,175 | A | 3/1998 | Rincoe |
| 5,728,176 | A | 3/1998 | Phillips |
| 5,728,177 | A | 3/1998 | Phillips |
| 5,746,774 | A | 5/1998 | Kramer et al. |
| 5,766,265 | A | 6/1998 | Phillips |
| 5,766,704 | A | 6/1998 | Allen et al. |
| 5,769,896 | A | 6/1998 | Rosendahl et al. |
| 5,776,205 | A | 7/1998 | Phillips |
| 5,779,735 | A | 7/1998 | Molino |
| 5,800,564 | A | 9/1998 | Gelineau |
| 5,800,565 | A | 9/1998 | Biedermann |
| 5,800,569 | A | 9/1998 | Phillips |
| 5,824,112 | A | 10/1998 | Phillips |
| 5,888,238 | A | 3/1999 | Phillips et al. |
| 5,893,891 | A | 4/1999 | Zahedi |
| 5,897,515 | A | 4/1999 | Willner et al. |
| 5,899,944 | A | 5/1999 | Phillips |
| 5,913,902 | A | 6/1999 | Geible |
| 5,944,679 | A | 8/1999 | DeToro |
| 5,944,760 | A | 8/1999 | Christensen |
| 5,957,981 | A | 9/1999 | Gramnas |
| 5,976,191 | A | 11/1999 | Phillips |
| 5,993,488 | A | 11/1999 | Phillips |
| 6,007,582 | A | 12/1999 | May |
| 6,019,741 | A | 2/2000 | Prieskorn |
| 6,019,795 | A | 2/2000 | Phillips |
| 6,071,313 | A | 6/2000 | Phillips |
| 6,077,301 | A | 6/2000 | Pusch |
| 6,083,184 | A | 7/2000 | Kenosh |
| 6,099,572 | A | 8/2000 | Mosler et al. |
| 6,120,547 | A | 9/2000 | Christensen |
| 6,165,227 | A | 12/2000 | Phillips |
| 6,187,052 | B1 | 2/2001 | Molino et al. |
| 6,197,068 | B1 | 3/2001 | Christensen |
| 6,206,934 | B1 | 3/2001 | Phillips |
| 6,228,124 | B1 | 5/2001 | Slemker et al. |
| 6,241,776 | B1 | 6/2001 | Christensen |
| 6,245,035 | B1 | 6/2001 | Schrijver |
| 6,254,643 | B1 | 7/2001 | Phillips |
| 6,261,324 | B1 | 7/2001 | Merlette |
| 6,267,742 | B1 | 7/2001 | Krivosha et al. |
| 6,280,479 | B1 | 8/2001 | Phillips |
| 6,290,730 | B1 | 9/2001 | Pitkin et al. |
| 6,302,858 | B1 | 10/2001 | DeToro et al. |
| 6,306,178 | B1 | 10/2001 | Kania et al. |
| D457,639 | S | 5/2002 | McCoy |
| 6,402,790 | B1 | 6/2002 | Celebi |
| 6,406,500 | B1 | 6/2002 | Phillips |
| 6,443,993 | B1 | 9/2002 | Koniuk |
| 6,443,995 | B1 | 9/2002 | Townsend et al. |
| 6,514,293 | B1 | 2/2003 | Jang et al. |
| 6,562,075 | B2 | 5/2003 | Townsend et al. |
| 6,596,029 | B1 | 7/2003 | Gramnas |
| 6,602,295 | B1 | 8/2003 | Doddroe et al. |
| 6,663,673 | B2 | 12/2003 | Christensen |
| 6,669,737 | B2 | 12/2003 | Mosler et al. |
| 6,676,618 | B2 | 1/2004 | Andersen |
| 6,676,708 | B1 | 1/2004 | Laghi |
| 6,740,125 | B2 | 5/2004 | Mosler |
| 6,767,370 | B1 | 7/2004 | Mosler et al. |
| 6,793,683 | B1 | 9/2004 | Laghi |
| 6,805,717 | B2 | 10/2004 | Christensen |
| 6,811,571 | B1 | 11/2004 | Phillips |
| 6,869,451 | B1 | 3/2005 | Laghi |
| 6,875,241 | B2 | 4/2005 | Christensen |
| 6,875,242 | B2 | 4/2005 | Christensen |

| | | |
|---|---|---|
| 6,887,213 B2 | 5/2005 | Smits |
| 6,887,279 B2 | 5/2005 | Phillips et al. |
| 6,899,737 B1 | 5/2005 | Phillips et al. |
| 6,911,052 B2 | 6/2005 | Christensen |
| 6,929,665 B2 | 8/2005 | Christensen |
| 6,942,702 B2 | 9/2005 | Mitsugi et al. |
| 6,945,947 B2 | 9/2005 | Ingimundarson et al. |
| 6,964,119 B2 | 11/2005 | Weaver, III |
| 6,966,933 B2 | 11/2005 | Christensen |
| 6,972,043 B1 | 12/2005 | Biedermann et al. |
| 7,077,818 B2 | 7/2006 | Ingimundarson et al. |
| 7,169,190 B2 | 1/2007 | Phillips |
| 7,172,630 B2 | 2/2007 | Christensen |
| 7,264,592 B2 | 9/2007 | Shehada |
| 7,266,910 B2 | 9/2007 | Ingimundarson |
| 7,279,011 B2 | 10/2007 | Phillips |
| 7,341,603 B2 | 3/2008 | Christensen |
| 7,347,877 B2 | 3/2008 | Clausen et al. |
| 7,354,456 B2 | 4/2008 | Phillips |
| 7,410,503 B2 | 8/2008 | Townsend et al. |
| 7,419,509 B2 | 9/2008 | Christensen |
| 7,462,201 B2 | 12/2008 | Christensen |
| 7,507,259 B2 | 3/2009 | Townsend et al. |
| 7,520,904 B2 | 4/2009 | Christensen |
| 7,572,299 B2 | 8/2009 | Christensen |
| 7,618,464 B2 | 11/2009 | Christensen |
| 7,686,848 B2 | 3/2010 | Christensen |
| 7,727,285 B2 | 6/2010 | Christensen |
| 7,740,602 B2 | 6/2010 | Christensen |
| 7,794,506 B2 | 9/2010 | Christensen |
| 7,811,334 B2 | 10/2010 | Ragnarsdottir et al. |
| 7,824,446 B2 | 11/2010 | Christensen |
| 2002/0077706 A1 | 6/2002 | Phillips |
| 2003/0120354 A1 | 6/2003 | Doddroe et al. |
| 2004/0243253 A1 | 12/2004 | Coole et al. |
| 2005/0038525 A1 | 2/2005 | Doddroe |
| 2005/0049721 A1 | 3/2005 | Sulprizio |
| 2005/0197717 A1 | 9/2005 | Ragnardottir et al. |
| 2005/0203640 A1 | 9/2005 | Christensen |
| 2005/0261783 A1 | 11/2005 | Geilman et al. |
| 2006/0030950 A1 | 2/2006 | Townsend |
| 2006/0069450 A1* | 3/2006 | McCarvill et al. ............... 623/55 |
| 2006/0241783 A1 | 10/2006 | Christensen |
| 2008/0167730 A1 | 7/2008 | Pusch |
| 2008/0312752 A1 | 12/2008 | Miller |
| 2009/0012630 A1* | 1/2009 | Mosler et al. .................... 623/55 |
| 2009/0265019 A1 | 10/2009 | Christensen |
| 2009/0281638 A1 | 11/2009 | Tourneux |
| 2010/0023135 A1 | 1/2010 | Rubie et al. |
| 2011/0009982 A1 | 1/2011 | King et al. |

FOREIGN PATENT DOCUMENTS

| | | |
|---|---|---|
| EP | 1 149 568 | 10/2001 |
| EP | 1340478 | 9/2003 |
| GB | 2244006 | 11/1991 |
| JP | 55112440 | 8/1980 |
| JP | 57040138 | 3/1982 |
| JP | 633231031 | 9/1988 |
| RU | 2033772 | 4/1995 |
| SU | 560606 | 6/1977 |
| WO | WO 94 10942 | 5/1994 |
| WO | WO03/003953 | 1/2003 |

OTHER PUBLICATIONS

PCT Application PCT/US2011/039607; filing date Jun. 8, 2011; International Search Report mailed Feb. 17, 2012.
Freedom Innovations; Freedom by Design, World-Class Carbon Fiber Foot Solutions; 2010; 11 pages.
U.S. Appl. No. 12/425,876, filed Apr. 17, 2009; Roland J. Christensen; Notice of Allowance issued Jul. 12, 2011.
U.S. Appl. No. 12/425,876, filed Apr. 17, 2009; Roland J. Christensen; office action issued May 27, 2011.
www.micacorp.com/products/genesis2/, MICA Manufacturing Corporation, Genesis II Prosthetic Foot, Nov. 24, 2004, 1 page.
www.Oandp.org/jpo/library/2000_01_009.asp, "Comparison of the Seattle Lite Foot and Genesis II Prosthetic Foot during walking and running." American Academy of Orthotists and Prosthetists, 2000, pp. 9-14, vol. 12 No. 1.

* cited by examiner

PROSTHETIC FOOT WITH FLOATING FOREFOOT KEEL

BACKGROUND

1. Field of the Invention

The present invention relates generally to prosthetic feet.

2. Related Art

Many individuals have lost a limb for various reasons including war, accident, or disease. In most instances these individuals are not only able to live relatively normal lives, but physically active lives as well. Oftentimes, these individuals are aided in their everyday lives by a prosthetic limb. The objective of prosthesis is to provide an artificial limb that simulates the function and natural feel of the replaced limb.

With respect to prosthetic feet, the development of a functional and natural artificial foot has been limited by material and imagination. Many designs have attempted to copy the anatomy of the foot or simulate its actions by replacing the bones and muscle with various mechanical simulation by replacing the entire foot with an energy storage element such as a spring. As the user steps onto the foot, the user's weight compresses the spring. As the user moves forward, the user's weight comes off the foot and the energy stored in the spring is used to propel the user forward.

Almost all of the past designs have focused on the major aspect of the prosthetic foot movement of the ankle or foot as it relates to walking or running. Few designs consider the lateral, or side to side rotation of the foot when the foot is used on varied or uneven terrain. It will be appreciated that the forefoot and heel of a natural foot rotates with a medial to lateral roll-over to accommodate variations in terrain or when participating in various sporting events. Most artificial feet of previous designs usually incorporate a unitary foot that is incapable of such lateral roll-over movement.

Some devices incorporate joints that allow plantar-dorsiflexion and lateral flexion of the foot relative to the leg. Unfortunately, these devices generally do not allow for lateral rotation of the foot relative to the ankle. Of devices that do allow lateral rotation, many unnaturally constrain the rotation, allow rotation only in discrete increments, or allow rotation in an unnatural manner. Such lateral rotation is desirable for many athletic activities such as golf, basketball, and other sports where lateral rotation of the foot relative to the ankle is desirable. Moreover, resilient resistance to such rotation is desirable to approximate the function of the human ankle.

SUMMARY OF THE INVENTION

It has been recognized that it would be advantageous to develop a prosthetic foot with a soft feel and more natural ankle rotation.

The invention provides a prosthetic foot with an attachment member to be coupled to a stump of an amputee. An elongated vertical fastener is coupled to the attachment member. A pair of bumpers is disposed on the fastener with an upper bumper disposed over a lower bumper. The bumpers include a flexible and resilient material, and store energy therein when compressed, and release the energy therefrom when released. An elongate forefoot spring is suspended between the upper and lower bumpers. The forefoot spring has an attachment end, and extends to a toe end positioned at a toe location of a natural foot. The forefoot spring includes a resilient material and is bendable to store energy in the forefoot spring when deflected and return the energy from the forefoot spring when released. A heel spring is suspended between an end of the fastener and the lower bumper. The heel spring has an attachment end, and extends to a heel end positioned at a heel location of a natural foot. The heel spring includes a resilient material, and is bendable to store energy in the heel spring when deflected and return the energy from the heel spring when released.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 1c is a top view of the prosthetic foot of FIG. 1a;

FIG. 6b is a top view of the prosthetic foot of FIG. 6a;

FIG. 6c is a front view of the prosthetic foot of FIG. 6a; and

FIG. 6d is a partial, cross-sectional schematic view of an insert and bumper of the prosthetic foot of FIG. 6a.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

As illustrated in FIGS. 1a-2d, a prosthetic foot, indicated generally at 10, in an example implementation in accordance with the invention is shown. Such a foot can provide inversion/eversion rotation (side-to-side, inward and outward) of the foot and heel/toe rotation (longitudinal, front and back) of the foot. In addition, such a foot can provide various degrees of stiffness response.

Figure 1A:
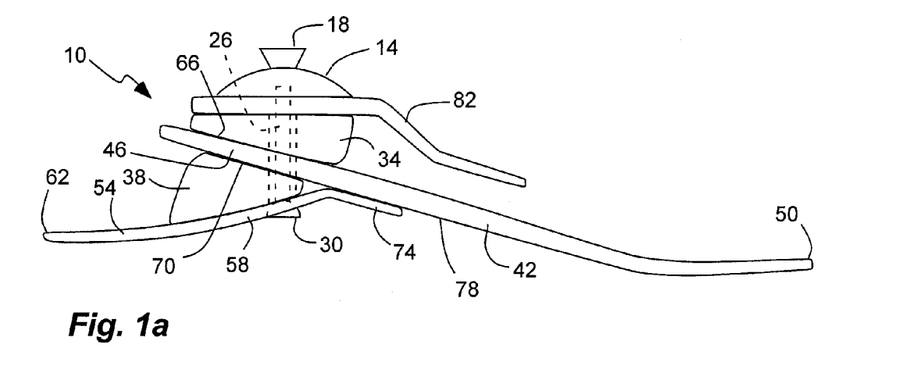
FIG. 1a is a side view of a prosthetic foot in accordance with an embodiment of the present invention.
Figure 1B:
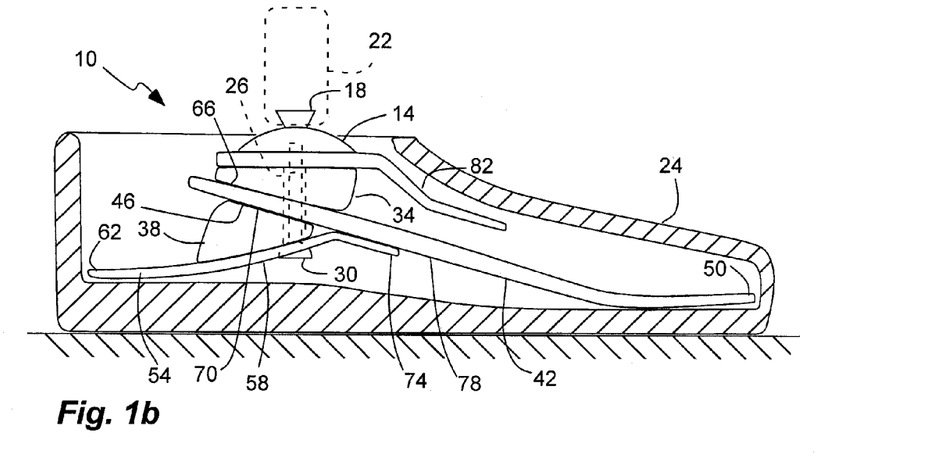
FIG. 1b is a side view of the prosthetic foot of FIG. 1a, shown with a cut-away cross-section of a shoe or shell, and shown in an unused, at-rest configuration with respect to a horizontal surface.
Figure 1C:
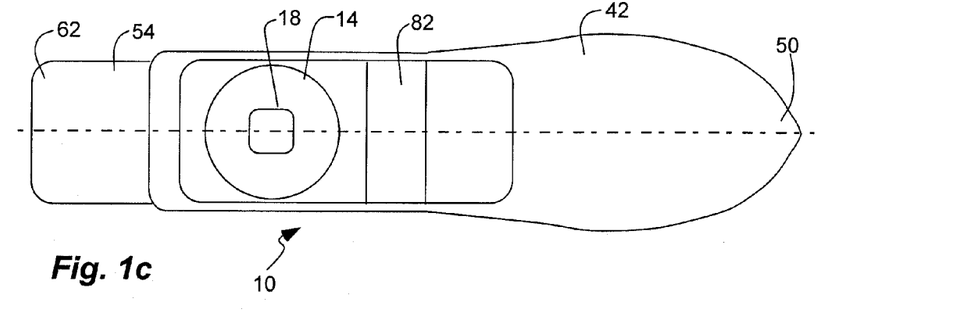
Figure 2A:
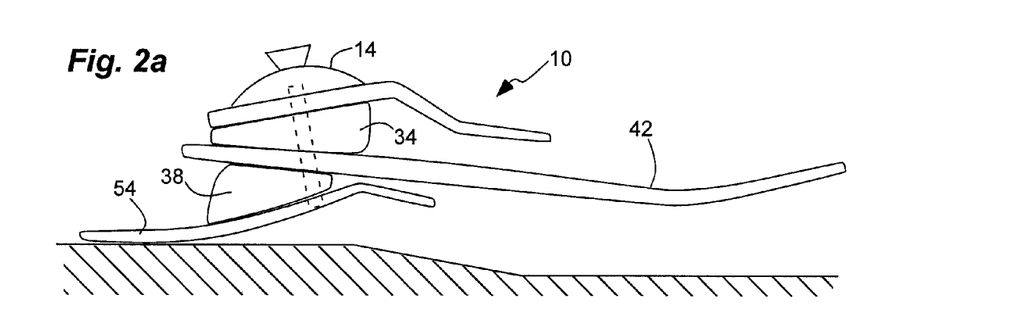
FIGS. 2a-d are side schematic views of the prosthetic foot of FIG. 1a illustrated in use with FIG. 2a depicting heel strike, FIG. 2b depicting mid stride or stance, FIG. 2c depicting toe-off, and FIG. 2d depicting toe-off in extreme use conditions.

The prosthetic foot 10 can have an attachment member 14 with an inverted pyramidal connector 18 (as is known in the art) coupled to a stump of an amputee, such as to a socket or pylon 22 (FIG. 2a). The foot can include a shell or can be disposed in a shoe, represented by 24, and which can provide an uneven surface, such as a higher heel with respect to the toe. An elongated vertical fastener 26 can be coupled to the attachment member 14. The fastener can extend to a head 30 spaced apart from and below the attachment member. The head can be semi-spherical or can have a semi-spherical or curved upper surface facing upward to the attachment member. The fastener can be a bolt or rod with a threaded end threaded into a threaded bore in a bottom of the attachment member.

A pair of bumpers can be disposed on the fastener 26, and can include an upper or forefoot bumper 34 and a lower or heel bumper 38. The upper bumper 34 can be disposed over the lower bumper 38. The bumpers 34 and 38 can have a vertical bore therethrough to receive the fastener therein so that the bumpers are carried by the fastener and coupled to the attachment member by the fastener. The bumpers can be discs or rings with the bore therein. The bumpers 34 and 38 can be formed of or can included a flexible and resilient material that stores energy therein when compressed, and releases the energy therefrom when released or uncompressed. The material can be or can include polyurethane. The stiffness of the upper and lower bumpers can be different with respect to one another.

An elongate forefoot keel or spring 42 is suspended between the upper and lower bumpers 34 and 38, or between the forefoot bumper and the heel bumper. The forefoot spring can have an attachment end 46 coupled to the attachment member 14. A bore can be formed through the attachment end of the forefoot spring so that the forefoot spring is carried by the fastener 26. The forefoot spring can extend to a toe end 50 positioned at a toe location of a natural foot. The forefoot spring can be a long flat member with a slight curvature that is formed of or includes a resilient material. The forefoot spring is bendable to store energy in the forefoot spring when deflected, and to return the energy from the forefoot spring when released or unloaded. For example, the forefoot spring can be a composite with fiber in a resin matrix. The upper or forefoot bumper 34 is disposed between, and compressible between, the attachment end 46 of the forefoot spring 42 and the attachment member 14.

A heel spring 54 can be suspended between the lower bumper 38 and the head 30 of the fastener 26. The heel spring can have an attachment end or section 58 coupled to the attachment member 14 and the forefoot spring 42. A bore can be formed through the attachment end or section 58 of the heel spring so that the heel spring is carried by the fastener 26. The heel spring 54 can extend to a heel end 62 positioned at a heel location of a natural foot. The heel spring 54 can be a long flat member with a slight curvature that is formed of a resilient material. The heel spring is bendable to store energy in the heel spring when deflected, and to return the energy from the heel member when released or unloaded. For example, the heel spring can be a composite with fiber in a resin matrix. The lower or heel bumper 38 is disposed between, and compressible between, the attachment ends 46 and 58 of the forefoot and heel springs 42 and 54.

A bore can extend through the heel spring 54, the heel bumper 38, the forefoot spring 42 and the forefoot bumper 34, or the bores thereof can be substantially aligned. The fastener 26 extends through the bore and is attached to the attachment member 14 such that the heel spring, the heel bumper, the forefoot spring and the forefoot bumper are carried by the fastener and secured to the attachment member by the fastener. The bore can be oversized with respect to the fastener, particularly for the forefoot and heel springs to allow pivoting. The forefoot and heel springs, and the forefoot and heel bumpers, (and the forefoot stop) can be held snugly between the attachment member 14 and the head 30 of the fastener 26 such that the forefoot and heel springs, and the forefoot and heel bumpers, (and the forefoot stop) or thicknesses thereof can completely fill the distance or gap between the attachment member and head. The fastener can even pre-load or pre-compress the bumpers.

Figure 2B:
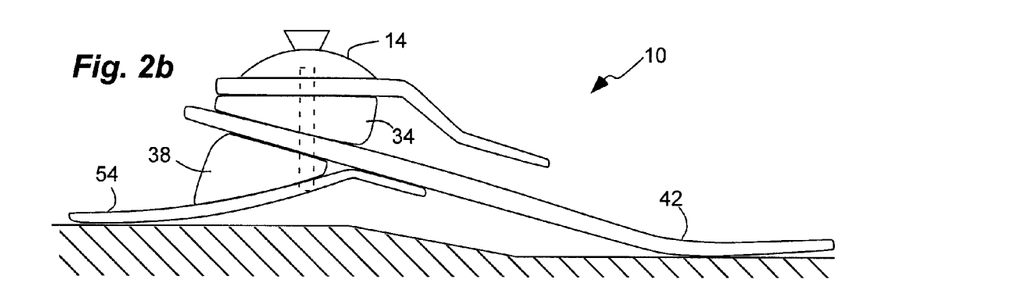
Figure 2C:
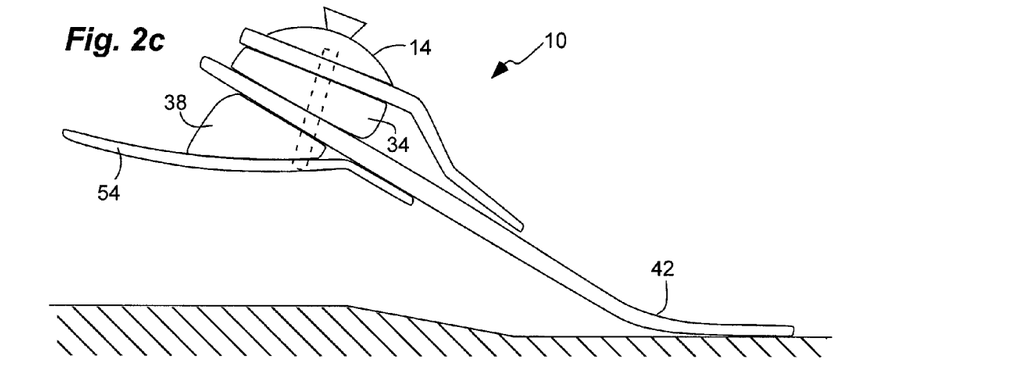

The upper or forefoot bumper 34 has a substantial wedge shape in profile (or from the side or in cross-section taken from a vertical plane through the longitudinal axis) when the foot is in an unused, at-rest configuration. The bumper 34 has a thinner rear end and a thicker front end, with the thickness measured vertically. The bottom of the attachment member and the top of the forefoot bumper can be substantially horizontal, when the foot is in an unused, at-rest configuration. A bottom 66 of the forefoot bumper 34 forms an acute angle with respect to horizontal when the foot is in an unused, at-rest configuration. Similarly, the attachment end 46 of the forefoot spring 42 can abut to the bottom 66 of the forefoot bumper 34, and is oriented at an acute angle between the forefoot and heel bumpers, when the device is in an unused, at-rest configuration. Thus, the forefoot is suspended between the bumpers at an acute angle. The rear end of the forefoot bumper 34 is compressed on heel strike, as shown in FIG. 2a. The front end of the forefoot bumper 34 is compressed on toe off, as shown in FIG. 2c. The entire forefoot bumper 34 can be compressed in mid-stride or stance or standing, as shown in FIG. 2b. In addition, the forefoot spring can bend during toe-off, as shown in FIG. 2c. Furthermore, the forefoot spring 42 can pivot on the fastener between the bumpers in a forward and rearward direction, or toe-to-heel direction, during use or gait. Similarly, the forefoot spring can pivot in a side-to-side, or inversion/eversion, direction during use to provide for a more natural ankle rotation.

The heel bumper 38 also has a substantial wedge shape in profile (or from the side or in cross-section taken from a vertical plane through the longitudinal axis) when the foot is in an unused, at-rest configuration. The wedge shapes of the forefoot and heel bumpers can have opposite orientations. The bumper 38 has a thicker rear end and a thinner front end, with the thickness measured vertically. A top 70 of the heel bumper 38 forms an acute angle with respect to horizontal, when the foot is in an unused, at-rest configuration. Again, the acute angles of the top of the lower bumper and the bottom of the upper bumper allow the attachment end of the forefoot member to be oriented at an acute angle. The rear end of the heel bumper is compressed on heel strike, as shown in FIG. 2a. A front end of the heel bumper is compressed on toe off, as shown in FIG. 2c. The entire heel bumper can be compressed in mid-stride or stance or standing, as shown in FIG. 2b. In addition, the heel spring can bend upon heel strike during use, as shown in FIG. 2a.

The attachment end 58 of the heel spring 54, or distal end or tab 74 thereof, can abut to an under side 78 of the forefoot spring 42 during toe off, as shown in FIG. 2c, and during mid-stride or stance or standing, as shown in FIG. 2b. The heel spring 54 can be spaced-apart from the forefoot spring 42 during heel strike, as shown in FIG. 2a, with the distal end or tab 74 separating away from the under side 78 of the forefoot spring. During heel strike, as shown in FIG. 2a, the heel spring 54 can pivot on the head 30 of the fastener 26 in a forward and rearward direction, or toe-to-heel direction. Similarly, the heel spring can pivot in a side-to-side, or inversion/eversion, direction during use to provide for a more natural ankle rotation.

Figure 2D:
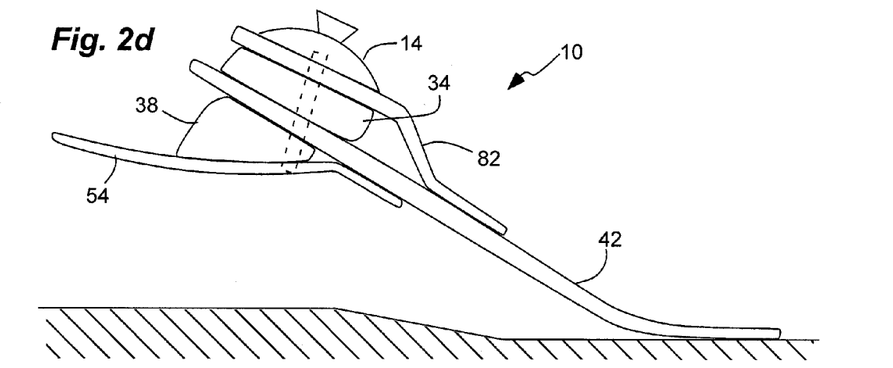

A forefoot stop 82 can be coupled to the attachment member 14 and disposed over and spaced above the forefoot spring 42. The forefoot spring 42 can bend or deflect into a space between the forefoot spring and the forefoot stop under normal use conditions, as shown in FIG. 2c. In addition, the forefoot spring can bend or deflect to abut to the forefoot stop under extreme use conditions, as shown in FIG. 2d. The forefoot stop 82 can be a rigid member that is substantially fixed without significant deflection. Alternatively, the forefoot stop can be replaced with a similarly shaped member that is a leaf spring similar to the forefoot spring that can deflect along with the forefoot spring, but providing greater resistance or stiffness.

As described above, the forefoot and heel springs can be relatively thin and substantially flat, with the forefoot and heel bumpers having a thickness greater than a thickness of the forefoot and heel springs.

Referring to FIGS. 2a-d, in use, the heel spring 54 can bend or deflect while the heel bumper 38 compresses on heel strike, as shown in FIG. 2a. The user's weight applied to the attachment member 14 can also cause the upper and the lower bumpers 34 and 38, or rear ends thereof, to compress on heel strike. At mid-stride, as shown in FIG. 2b, both bumpers can be compressed between the attachment member and the heel spring, with both the heel and forefoot springs bending or deflecting. As the user strides forward, as shown in FIG. 2b, the heel spring can return the energy stored on heel strike. On toe-off, as shown in FIG. 2c, the forefoot spring 42 can bend or deflect while the upper bumper 34 compresses. As the user lifts off, the forefoot spring can return the energy stored as the user strode forward. As shown in FIG. 2d, the forefoot spring 42 can abut to the forefoot stop 82 under greater force. In addition, on uneven terrain, the heel and forefoot springs 54 and 42 can pivot or rotate side-to-side, or with inversion/eversion, under resistance from the bumpers, to provide a more natural ankle rotation.

Figure 3:
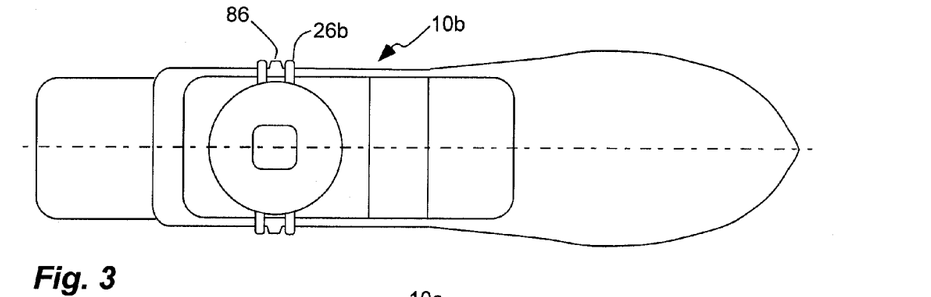
FIG. 3 is a top view of another prosthetic foot in accordance with another embodiment of the present invention.

Referring to FIG. 3, another prosthetic foot 10b is shown that is similar in most respects to that described above, and which description is herein incorporated by reference, but with a fastener 26b that extends around the lateral side, rather than through, the members (forefoot and heel springs and bumpers). The members can have a tab 86 keyed in a slot in the fastener to help retain the members. The slot can be vertically oriented with the tabs capable of moving vertically in the slot as the members compress. In addition, the members can pivot about the tab in the slot.

Figures 4, 5:
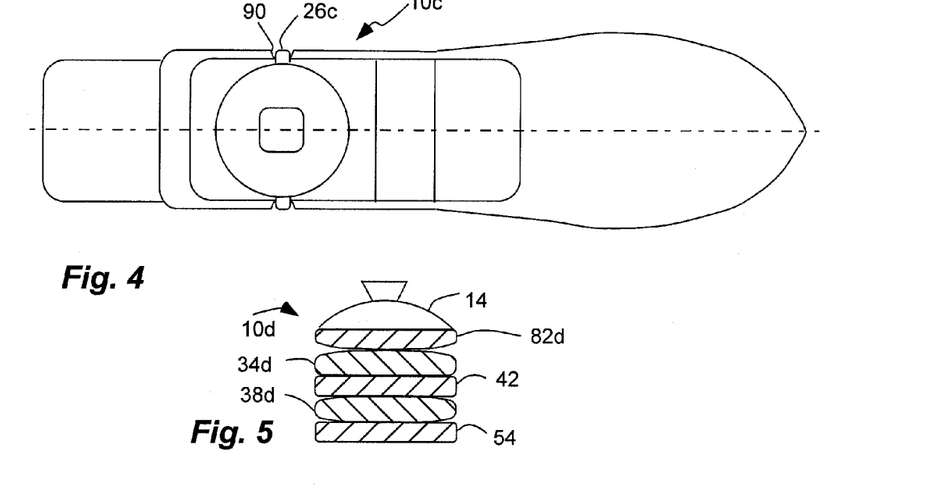
FIG. 4 is a top view of another prosthetic foot in accordance with another embodiment of the present invention.
FIG. 5 is a cross-sectional end view of another prosthetic foot in accordance with another embodiment of the present invention.

Referring to FIG. 4, another prosthetic foot 10c is shown that is similar in most respects to that described above, and which description is herein incorporated by reference, but with a fastener 26c that extends around the lateral side, rather than through, the members (forefoot and heel springs and bumpers). The members can have a notch 90 receiving the fastener to help retain the members. The members can pivot about the notch.

Referring to FIG. 5, another prosthetic foot 10d is shown that is similar in most respects to that described above, and which description is herein incorporated by reference, but with members (attachment member, forefoot and heel springs and bumpers) that can have curved surfaces to facilitate side-to-side, or inversion/eversion, rotation. The curvature can be in the side-to-side or lateral direction. For example, a bottom of the attachment member 14 or forefoot stop 82d can have a curved lower surface. Alternatively, or in addition, the top surface of the upper bumper 34d can have a curved upper surface. Similarly, the upper and/or lower surfaces of the lower bumper 38d can be curved.

Referring to FIGS. 6a-6d, another prosthetic foot 10e is shown that is similar in post respects to those described above, and which description is herein incorporated by reference. The prosthetic foot 10e has a pair of bumpers including an upper or forefoot bumper 34e and a lower or heel bumper 38e. The bumpers 34e and 38e can be formed of or can include a flexible and resilient material that stores energy therein when compressed, and releases the energy therefrom when released or uncompressed. The material can be or can include polyurethane. The stiffness of the upper and lower bumpers can be different with respect to one another.

Figure 6A:
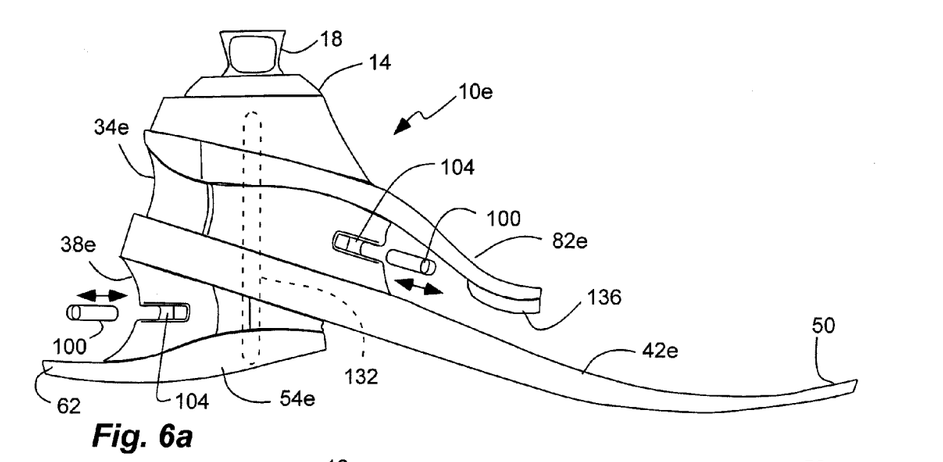
FIG. 6a is a side view of another prosthetic foot in accordance with another embodiment of the present invention.
Figure 6B:
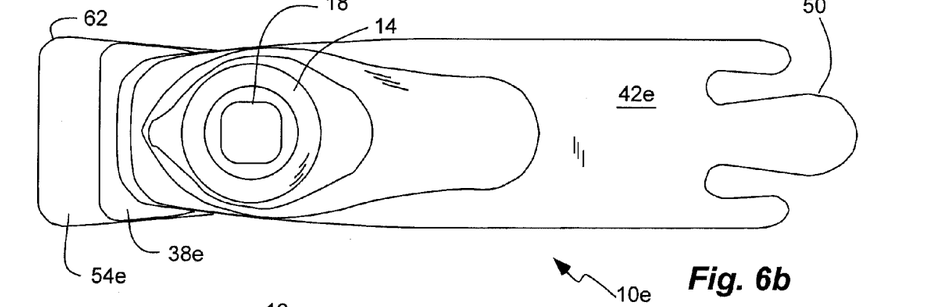
Figure 6C:
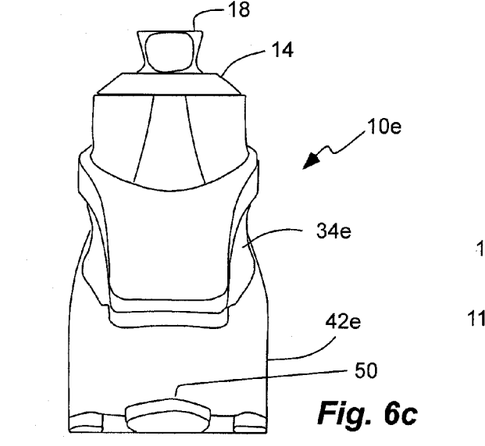
Figure 6D:
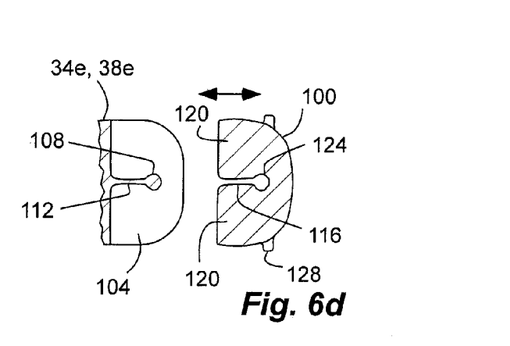

In addition, the stiffness of the upper and lower bumpers can be varied with a stiffness insert 100 that can have a different characteristic, such as stiffness, than the bumpers. The stiffness insert 100 can be removeably or replaceably disposed in a notch 104 formed in the bumpers. The notch 104 can be formed in the front of the upper bumper and the rear of the lower bumper. The notch 104 can extend a width of the bumpers and can be intermediate a thickness of the bumpers. The stiffness insert 100 can snap-fit into the notch 104. For example, the notch 104 can have an enlarged head or column 108 traversing a thickness of the notch and a narrower neck 112. The stiffness insert 100 can have a slot 116 formed between a pair of arms 120. The insert and arms can be flexible to expand as pushed passed the head or column 108, and resilient to collapse about the head or column and neck to maintain the insert in the notch. The insert can also have an enlarged cavity 124 at the end of the slot to receive the enlarged head. The insert 100 can have a thickness equal to a thickness of the notch. As described above, the insert 100 can have a greater or lesser stiffness than that of the bumpers, and various different inserts can be provided with different stiffness, so that the stiffness of the bumpers, or combined bumpers and inserts, produce the desired stiffness and comfort. Lateral wings or tabs 128 can extend from the insert to facilitate grasping and removal of the insert for replacement. The stiffness insert can also be formed of polyurethane.

An elongate forefoot keel or spring 42e is suspended between the upper and lower bumpers 34e and 38e, or between the forefoot bumper and the heel bumper. The forefoot spring can be a long flat member with a slight curvature that is formed of or includes a resilient material. The forefoot spring is bendable to store energy in the forefoot spring when deflected, and to return the energy from the forefoot spring when released or unloaded. For example, the forefoot spring can be a composite with fiber in a resin matrix. The upper or forefoot bumper 34e is disposed between, and compressible between, the attachment end of the forefoot spring 42e and the attachment member 14.

A heel spring 54e can be suspended on a bottom of the lower bumper 38e. The heel spring can have an attachment end or section coupled to the attachment member 14 and the forefoot spring 42e. The heel spring 54 can be a long flat member with a slight curvature that is formed of a resilient material. The heel spring is bendable to store energy in the heel spring when deflected, and to return the energy from the heel member when released or unloaded. For example, the heel spring can be a composite with fiber in a resin matrix. The lower or heel bumper 38e is disposed between, and compressible between, the attachment ends of the forefoot and heel springs 42e and 54e.

The bumpers 34e and 38e, the forefoot spring 42e and the heel spring 54e can be coupled to the attachment member 14 by a fastener, such as a cable 132. The cable can be flexible to allow movement about the compressible bumpers. The heel spring 54e can be suspended between the bumper 38e and an end of the fastener or cable. The cable can extend through one or more bores.

A bumper 136 can also be disposed between the forefoot spring 42e and the forefoot stop 82e.

As described above, the fasteners can be releasably attached to the attachment member so that the bumpers can be removed and replaced with bumpers having different stiffness so that the foot or feel of the foot can be customized to the user. In addition, stiffer bumpers and/or stiffer springs can be used for heavier users.

The phrase unused, at-rest configuration of the foot is intended to refer to the foot unloaded, unused, and at-rest in its intended use either in a shoe or shell, or on a surface.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A prosthetic foot device, comprising:
   a) an attachment member configured to be coupled to a stump of an amputee;
   b) a forefoot stop coupled to the attachment member at a rear attachment end and having a free forward stop end cantilevered forwardly from the rear attachment end;
   c) an elongate forefoot spring having a rear spring attachment end coupled to the attachment member and extending to a toe end positioned at a toe location of a natural foot, the forefoot spring including a resilient material and bendable to store energy in the forefoot spring when deflected and return the energy from the forefoot spring when released;
   d) the forefoot stop being spaced above the forefoot spring, the forefoot spring being bendable into a space between the forefoot spring and the forefoot stop under normal use conditions, and the forefoot spring being bendable to abut to the forefoot stop under extreme use conditions;
   e) a forefoot bumper disposed between and compressible between the rear spring attachment end of the forefoot spring and the rear attachment end of the forefoot stop, the forefoot bumper including a flexible and resilient material and storing energy in the forefoot bumper when compressed and releasing the energy from the forefoot bumper when released;
   f) a heel spring having a front attachment end coupled to the rear spring attachment end of the forefoot spring and coupled to the attachment member and extending to a heel end positioned at a heel location of a natural foot, the heel spring including a resilient material and bendable to store energy in the heel spring when deflected and return the energy from the heel spring when released;
   g) a heel bumper disposed between and compressible between the attachment ends of the forefoot and heel springs, the heel bumper including a flexible and resilient material and storing energy in the heel bumper when compressed and releasing the energy from the heel bumper when released;
   h) the heel spring bending and the heel bumper compressing upon heel strike during use; and the forefoot spring bending and the forefoot bumper compressing during toe-off;
   i) a fastener coupling the heel spring the forefoot spring to the attachment member, the fastener extending through the front attachment end of the heel spring, through the heel bumper, through the rear spring attachment end of the forefoot spring, through the forefoot bumper, through the rear attachment end of the forefoot stop, and into the attachment member.

2. A device in accordance with claim 1, wherein the forefoot spring is suspended between the forefoot bumper and the heel bumper.

3. A device in accordance with claim 1, wherein the forefoot bumper has a substantial wedge shape when the device is in an unused, at-rest configuration with a thinner rear end and a thicker front end; wherein the rear end of the forefoot bumper is compressed on heel strike; and wherein the front end of the forefoot bumper is compressed on toe off.

4. A device in accordance with claim 1, wherein the heel bumper has a substantial wedge shape when the device is in an unused, at-rest configuration with a thicker rear end and a thinner front end; wherein the rear end of the heel bumper is compressed on heel strike; and wherein the front end of the heel bumper is compressed on toe off.

5. A device in accordance with claim 1, wherein the front attachment end of the heel spring abuts to an under side of the forefoot spring during toe off; and
   wherein the heel spring is spaced-apart from the forefoot spring during heel strike.

6. A device in accordance with claim 1, wherein:
   the forefoot bumper is disposed over the heel bumper;
   the forefoot bumper has a bottom forming an acute angle with respect to horizontal when the device is in an unused, at-rest configuration;
   the heel bumper has a top forming an acute angle with respect to horizontal, when the device is in an unused, at-rest configuration; and
   the rear spring attachment end of the forefoot spring is oriented at an acute angle between the forefoot and heel bumpers when the device is in an unused, at-rest configuration.

7. A device in accordance with claim 1, wherein the forefoot and heel bumpers have a thickness greater than a thickness of the forefoot and heel springs.

8. A device in accordance with claim 1, further comprising:
   a notch formed in at least one of the forefoot and heel bumpers; and
   an insert removably disposed in the notch, the insert having a different stiffness than the at least one of the forefoot and heel bumpers.

9. A device in accordance with claim 1, further comprising:
   the forefoot stop having a greater resistance or stiffness than the forefoot spring, the forefoot stop extending forwardly from a portion near the attachment member toward the toe end of the forefoot spring and downwardly toward the forefoot spring.

10. A device in accordance with claim 1, further comprising:
    wherein the fastener further comprises a head having a curved upper surface which abuts a bottom surface of the heel spring.

11. A prosthetic foot device, comprising:
    a) an attachment member configured to be coupled to a stump of an amputee;
    b) a forefoot stop coupled to the attachment member and having a rear attachment end coupled to the attachment member and a free forward end;
    c) an elongate forefoot spring having a rear spring attachment end coupled to the attachment member and extending to a toe end positioned at a toe location of a natural foot, the forefoot spring including a resilient material and bendable to store energy in the forefoot spring when deflected and return the energy from the forefoot spring when released;
    d) the free forward end of the forefoot stop being cantilevered forward and disposed over and spaced above the forefoot spring, the forefoot spring being bendable into a space between the forefoot spring and the forefoot stop under normal use conditions, and the forefoot spring being bendable to abut to the forefoot stop under extreme use conditions;

e) a forefoot bumper disposed between and compressible between the attachment end of the forefoot spring and the rear attachment end of the forefoot stop, the forefoot bumper including a flexible and resilient material and storing energy in the forefoot bumper when compressed and releasing the energy from the forefoot bumper when released, the forefoot bumper having a substantial wedge shape when the device is in an unused, at-rest configuration with a thinner rear end and a thicker front end;

f) a heel spring having a forward attachment end coupled to the forefoot spring and attachment member and extending to a heel end positioned at a heel location of a natural foot, the heel spring including a resilient material and bendable to store energy in the heel spring when deflected and return the energy from the heel spring when released;

g) a heel bumper disposed between and compressible between the rear spring attachment end of the forefoot spring and the forward attachment end of the heel spring, the heel bumper including a flexible and resilient material and storing energy in the heel bumper when compressed and releasing the energy from the heel bumper when released, the heel bumper having a substantial wedge shape when the device is in an unused, at-rest configuration with a thicker rear end and a thinner front end;

h) the forefoot spring is suspended between the forefoot bumper and the heel bumper with the forefoot bumper disposed over the heel bumper;

i) the rear end of the forefoot bumper being compressed on heel strike, and the front end of the forefoot bumper being compressed on toe off;

j) a fastener extending from a bottom of the heel spring, extending through the forward attachment end of the heel spring, through the heel bumper, through the rear spring end of the forefoot spring, through the forefoot bumper, through the rear attachment end of the forefoot stop, and embedded into the attachment member such that the heel spring, the heel bumper, the forefoot spring, and the forefoot bumper are being carried by the fastener and secured to the attachment member by the fastener;

k) the forefoot bumper has a bottom forming an acute angle with respect to horizontal when the device is in an unused, at-rest configuration;

l) the heel bumper has a top forming an acute angle with respect to horizontal, when the device is in an unused, at-rest configuration; and m) the attachment end of the forefoot spring is oriented at an acute angle between the forefoot and heel bumpers when the device is in an unused, at-rest configuration.

12. A device in accordance with claim 11, wherein the forward attachment end of the heel spring abuts to an underside of the forefoot spring during toe off; and
wherein the heel spring is spaced-apart from the forefoot spring during heel strike.

13. A device in accordance with claim 11, wherein the forefoot and heel bumpers have a thickness greater than a thickness of the forefoot and heel springs.

14. A device in accordance with claim 11, further comprising:
a notch formed in at least one of the forefoot and heel bumpers; and
an insert removably disposed in the notch, the insert having a different stiffness than the at least one of the forefoot and heel bumpers.

15. An device in accordance with claim 11, further comprising
wherein the fastener further comprises a head having a curved upper surface which abuts a bottom surface of the heel spring.

16. A prosthetic foot apparatus comprising:

a) a heel spring having a top surface, a bottom surface, a rear spring portion located at a heel position of a natural foot, and a forward attachment end wherein the heel spring includes a resilient material and bendable to store energy in the heel spring when deflected and return the energy from the heel spring when released;

b) a heel bumper having a top surface and a bottom surface wherein the bottom surface of the heel bumper abuts the upper surface of the heel spring at the forward attachment end of the heel spring, the heel bumper including a flexible and resilient material and storing energy therein when compressed and releasing the energy therefrom when released;

c) an elongate forefoot spring having a top surface, a bottom surface, a forward toe portion extending to a toe position of a natural foot, and a rear spring attachment end wherein the bottom surface of the forefoot spring abuts against the top surface of the heel bumper at the rear spring attachment end of the forefoot spring, the forefoot spring including a resilient material and bendable to store energy in the forefoot spring when deflected and return the energy from the forefoot spring when released;

d) a forefoot bumper having a top surface and a bottom surface, wherein the bottom surface of the forefoot bumper abuts against the top surface of the forefoot spring, the forefoot bumper including a flexible and resilient material and storing energy therein when compressed and releasing the energy therefrom when released;

e) a forefoot stop having a bottom surface, a forward free end, and a rear connection end, wherein the bottom surface of the forefoot stop abuts the top surface of the forefoot bumper at the rear connection end;

f) an attachment member configured to be affixed to the stump of an amputee having an attachment device on a top of the attachment member and a bore on a bottom of the attachment member;

g) the forward free end of the forefoot stop is cantilevered forward above the top surface of the forefoot spring leaving a space between the forward free end of the forefoot stop and the forefoot spring under normal loads on the forefoot spring, the forefoot spring being bendable into the space between the forefoot spring and the forefoot stop under normal use conditions, and the forefoot spring being bendable to abut to the forefoot stop under extreme use conditions where the forefoot spring is configured to gain additional rigidity from the forefoot stop;

h) a fastener having an attachment end and having a head having a curved upper surface, wherein the head having a curved upper surface abuts the bottom surface of the heel spring and extends from the bottom surface of the heel spring at the forward attachment end, through the forward attachment end of the heel spring, through the heel bumper, through the forefoot spring at the rear spring attachment end of the forefoot spring, through the forefoot bumper, through the forefoot stop at the rear attachment end of the forefoot stop, and the attachment end is affixed into the bore on the bottom surface of the attachment member, wherein the fastener is configured to maintain the position of each element of the prosthetic foot apparatus in relation to the attachment member.

17. An apparatus in accordance with claim 16, wherein the forefoot bumper has a substantial wedge shape when the device is in an unused, at-rest configuration with a thinner rear end and a thicker front end; wherein the rear end of the forefoot bumper is compressed on heel strike; and wherein the front end of the forefoot bumper is compressed on toe off; wherein the heel bumper has a substantial wedge shape when the device is in an unused, at-rest configuration with a thicker rear end and a thinner front end; wherein the rear end of the heel bumper is compressed on heel strike; and wherein the front end of the heel bumper is compressed on toe off.

18. An apparatus in accordance with claim 16, wherein the forward attachment end of the heel spring abuts to the bottom surface of the forefoot spring during toe off; and wherein the heel spring is spaced-apart from the forefoot spring during heel strike.

19. An apparatus in accordance with claim 16, wherein:
the forefoot bumper has a bottom forming an acute angle with respect to horizontal when the apparatus is in an unused, at-rest configuration;
the top surface of the heel bumper has forms an acute angle with respect to horizontal, when the device is in an unused, at-rest configuration; and
the rear spring attachment end of the forefoot spring is oriented at an acute angle between the upper and lower bumpers when the device is in an unused, at-rest configuration.

20. An apparatus in accordance with claim 16, wherein the forefoot bumper and the heel bumper have a thickness greater than a thickness of the forefoot and heel springs.

21. An apparatus in accordance with claim 16, further comprising:
a notch formed in at least one of the forefoot bumper or the heel bumper; and
an insert removably disposed in the notch, the insert having a different stiffness than both the forefoot bumper and the heel bumper.

* * * * *